June 20, 1972 M. L. HANCOCK Plant Pat. 3,211
EUONYMUS FORTUNEI SHRUB
Filed Oct. 12, 1970
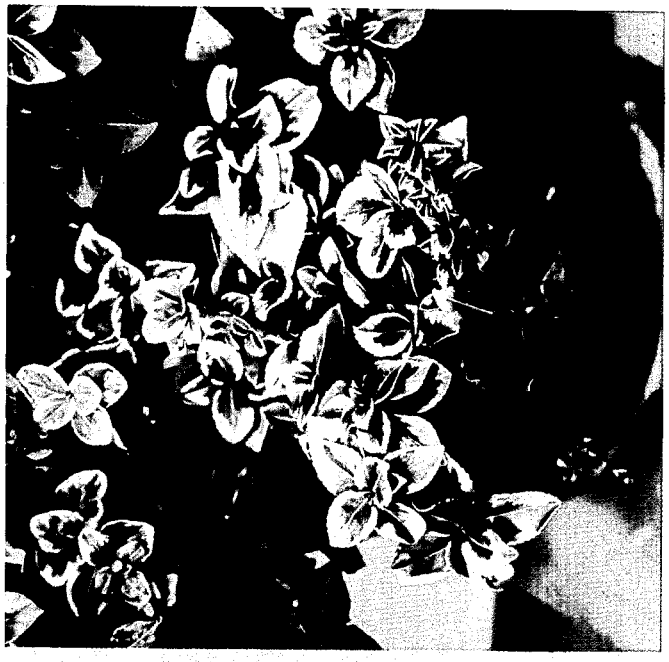
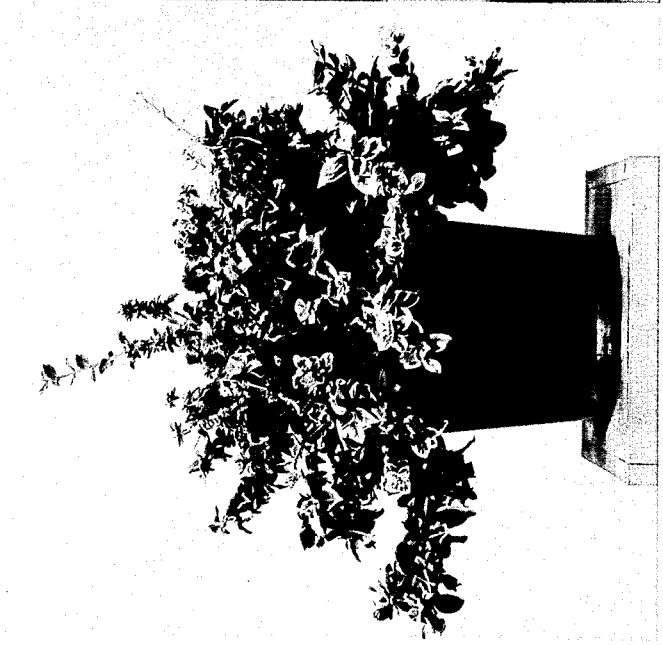
INVENTOR.
M. LESLIE HANCOCK,
By Edward F. Shanahan
ATTORNEY.

United States Patent Office

Plant Pat. 3,211
Patented June 20, 1972

3,211
*EUONYMUS FORTUNEI* SHRUB

M. Leslie Hancock, Cooksville, Ontario, Canada, assignor to Monrovia Nursery Company Filed Oct. 12, 1970, Ser. No. 80,255
Int. Cl. A01h *5/00*
U.S. Cl. Plt.—63 1 Claim The present invention relates to a new and distinct variety of the genus Euonymus, characterized as to novelty by its variegated foliage, its compact habit of growth, its ability to retain its foliage at temperatures of 20 degrees below zero, and its general usefulness as a foundation shrub in landscaping.

I first discovered the plant in August 1960, when it appeared as a sport among several *Euonymus fortunei* "Sarcoxie."

All present plants have been reproduced asexually from the original plant of August 1960. The plant has been asexually reproduced by me by means of cuttings. Cuttings have been taken from the original plant and all subsequent propagation has been from plants grown from these cuttings. All descendants have shown the same characteristics as the original plant, indicating that the new variety is thereby well established. The plant does not produce true from seed.

The new variety does not resemble its parent, but has a more compact growth and more variation in green and yellow foliage coloration.

A plant of the new variety, and an enlarged close-up view of some branches thereof, are shown in full color in the accompanying illustration.

A detail description of the new variety follows, and to facilitate identification of the important colors, the color terminology adopted by the British Horticultural Colour Charts has been followed.

*The plant*

Parentage: The plant first appeared as a sport of *Euonymus fortunei* "Sarcoxie," a non-patented variety.

Growth habit: The shrub exhibits a low growing compact habit with trailing branches. The branches will form rootlets and thus allow the plant to be trained along walls or other upright structures. The trailing branches will form a mat of from twelve to eighteen inches high.

Branches: The branches are basically upright and spreading, with lateral spreading branches developing adventitious roots. The young branches are scabrous and light green in appearance, with bark appearing dark green on the older wood. The plant does not develop a single stem. The branching is opopsite.

Foliage: The foliage is of fine texture, glossy, evergreen, and opposite. The mature leaves are 1⅛ to 1½ inches long and ¾ to 1 inch wide, broadly ovate to elliptical, and crenate, with broadly acute apices and obtuse bases. Petioles are ⅛ to 3/16 inches long. The leaves are dark green (Spinach Green 0960/1) with variegated margins of gold (Aureolin 3/1) and silver (Barium Yellow 503/1). Some leaves also appear entirely green or yellow. The undersides of the new mature leaves appear Spinach Green 0960/2.

I claim:

1. A new and distinct variety of *Euonymus fortunei* characterized by its compact growth and unusual range of foliage coloration, and by hardiness at below-freezing temperatures superior to plants most closely related to it.

No references cited.

ROBERT W. BAGWILL, Primary Examiner